United States Patent [19]
Odagiri et al.

[11] Patent Number: 6,129,676
[45] Date of Patent: *Oct. 10, 2000

[54] MOVEMENT RATE MONITOR

[75] Inventors: Hiroshi Odagiri; Keisuke Tsubata; Chiaki Nakamura; Kazumi Sakumoto; Naokatsu Nosaka, all of Chiba; Motomu Hayakawa, Suwa, all of Japan

[73] Assignee: Seiko Instruments Inc., Japan

[*] Notice: This patent issued on a continued prosecution application filed under 37 CFR 1.53(d), and is subject to the twenty year patent term provisions of 35 U.S.C. 154(a)(2).

[21] Appl. No.: 08/918,201

[22] Filed: Aug. 25, 1997

Related U.S. Application Data

[62] Division of application No. 08/355,503, Dec. 14, 1994, Pat. No. 5,697,374.

[30] Foreign Application Priority Data

Dec. 20, 1993 [JP] Japan .................................. 5-320157
Dec. 6, 1994 [JP] Japan .................................. 6-302511

[51] Int. Cl.⁷ .................................................. A61B 05/00
[52] U.S. Cl. ........................................... 600/500; 600/503
[58] Field of Search ............................. 600/485, 500–503

[56] References Cited

U.S. PATENT DOCUMENTS

| | | | |
|---|---|---|---|
| 5,025,791 | 6/1991 | Niwa | 128/670 |
| 5,431,170 | 7/1995 | Mathews | 600/500 |
| 5,494,043 | 2/1996 | O'Sullivan et al. | 600/500 |

FOREIGN PATENT DOCUMENTS

3150925 12/1981 Germany .

*Primary Examiner*—Robert L. Nasser
*Attorney, Agent, or Firm*—Adams & Wilks

[57] ABSTRACT

A movement rate monitor comprises extraction circuitry for extracting a selected movement frequency component from a power spectrum output of a movement sensor, and a movement rate calculation circuit for calculating movement rate in accordance with the extracted frequency component. A display device may be included to display the calculated movement rate.

4 Claims, 14 Drawing Sheets

FIG. 14 ns is a divisional of U.S. Ser. No. 08/355,
MOVEMENT RATE MONITOR

This application is a divisional of U.S. Ser. No. 08/355,503, filed Dec. 14, 1994, now U.S. Pat. No. 5,697,374.

BACKGROUND OF THE INVENTION

The present invention relates to a pulse rate monitor and a movement rate monitor capable of being mounted on a portion of a human or biological body.

Figure 11:
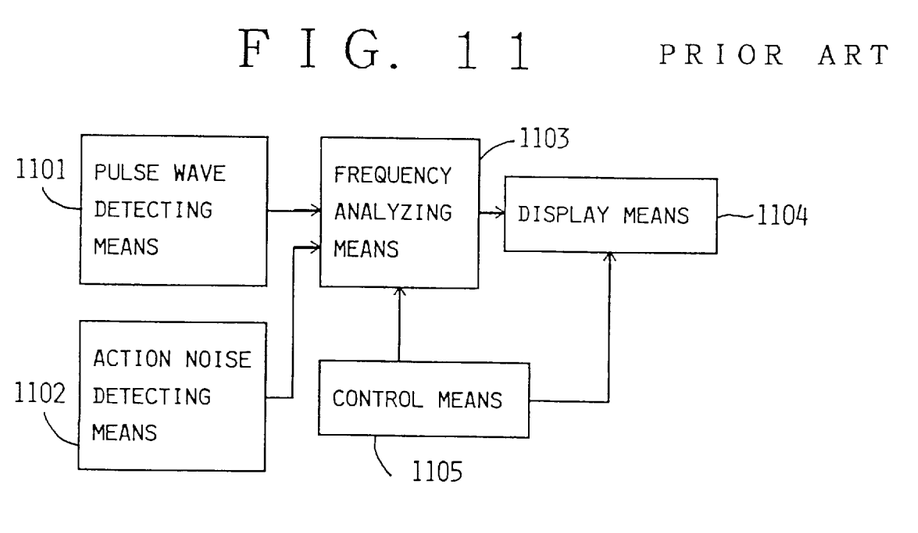
FIG. 11 is a functional block diagram for indicating the arrangement of the conventional pulse rate monitor.

FIG. 11 is a functional block diagram for representing the construction of the conventional pulse wave detecting apparatus. The pulse wave detecting means 1101 detects the pulse wave signal, and outputs the detected pulse wave signal to the frequency analyzing means 1103. The action noise (i.e., movement) detecting means 1102 detects the action noise, or movement, signal and outputs the detected action noise signal to the frequency analyzing means 1103. The display means 1104 displays the frequency-analyzed result generated by the frequency analyzing means 1103. The control means 1105 controls the frequency analyzing means 1103 and the display means 1104.

The above-described pulse wave analyzing apparatus is disclosed in Japanese Laid-open Patent No. 60-259239.

However, the conventional pulse rate monitor merely displays both the frequency analyzed result of the pulse wave sensor and the frequency analyzed result of the action noise sensor on the output display unit. As a result, either the pulse wave frequency, or the pulse rate are specified by the user while observing the respective result representations. Also, the signals are calculated in the same signal processing system with respect to the stationary condition and the action condition, and thus, the unnecessary signal processing unit is operated even under the stationary condition.

SUMMARY OF THE INVENTION

It is an object of the present invention to provide a pulse rate monitor capable of displaying a final output as a pulse rate representation even under the motion condition. Furthermore, another object of the present invention is to provide such a pulse rate monitor with the capability of suppressing power consumption by reducing the calculations performed on a signal under a stationary condition, thereby shortening calculation time.

To achieve the above-described objects, in accordance with the present invention, a pulse rate monitor is arranged by employing pulse wave component extracting means for extracting pulse wave components from frequency analyzing results of a pulse wave sensor and an action noise sensor; and pulse rate calculating means for calculating a pulse rate based on the pulse wave components extracted from the pulse wave component extracting means. Further, the pulse rate monitor is arranged by confirming whether or not the action noise signal exists by action noise detecting means; and for changing the calculation method using a calculation changing means when no action noise signal exists during a predetermined period of time. As a result, the calculation amount can be reduced and the power consumption can be suppressed, so that the calculation time can be shortened.

BRIEF DESCRIPTION OF THE DRAWINGS

FIGS. 12A–12C are explanatory diagrams for indicating examples of output appearance of the pulse rate monitor according to the present invention, in which FIG. 12A is an example in which the pulse rate monitor has a pulse wave sensor of the finger type, FIG. 12B is an example in which the action noise sensor is arranged into the user's belt, and FIG. 12C is an example in which the pulse wave sensor and the action noise sensor are arranged on a watch strap;

DETAILED DESCRIPTION OF THE PREFERRED EMBODIMENTS

Figure 1:
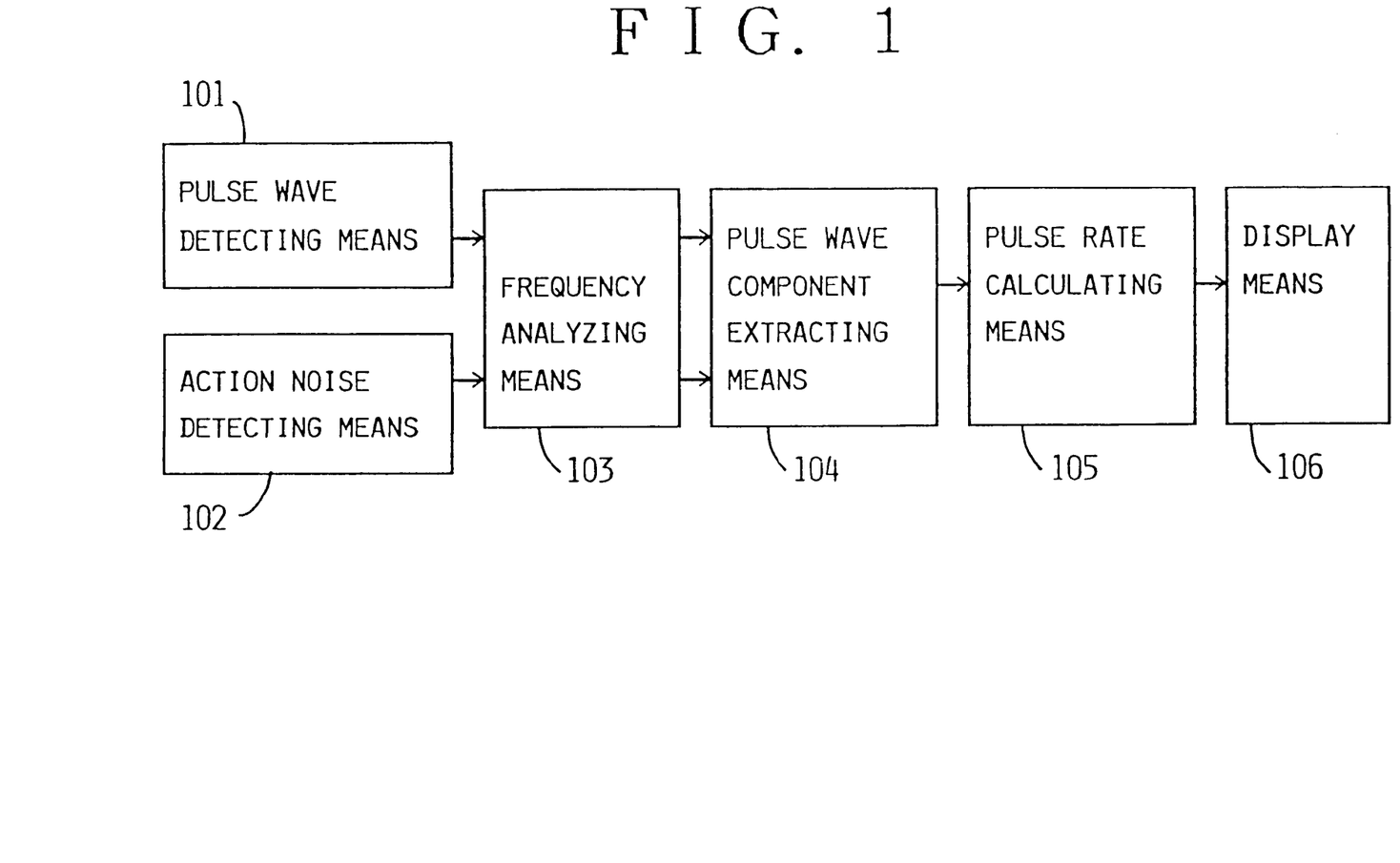
FIG. 1 is a functional block diagram for representing an example of a first embodiment of the pulse rate monitor of the present invention.

Referring now to the drawings, preferred embodiments of the present invention will be described as follows:

FIG. 1 is a functional block diagram for representing a first embodiment of the pulse rate monitor according to the present invention.

The pulse wave detecting means 101 detects a pulse wave from a human body and outputs the detected signal to the frequency analyzing means 103. The action noise detecting means 102 detects a movement of the human body and outputs the detected signal to the frequency analyzing means 103. The frequency analyzing means 103 frequency-analyzes the output signals from the pulse wave detecting means 101 and the action noise detecting means 102. To perform the frequency analysis, for instance, the Fast Fourier Transform is employed.

The pulse wave component extracting means 104 specifies a pulse wave component corresponding to a pulse rate frequency from the frequency-analyzed results outputted from the pulse wave detecting means 101 and the action noise detecting means 102, and outputs the specified pulse wave component to the pulse rate calculating means 105. The pulse rate calculating means 105 calculates a pulse rate per minute from the frequency component of the pulse rate specified by the pulse wave component extracting means 104. The display means 106 displays the pulse rate calculated by the pulse rate calculating means 105.

Figure 2:
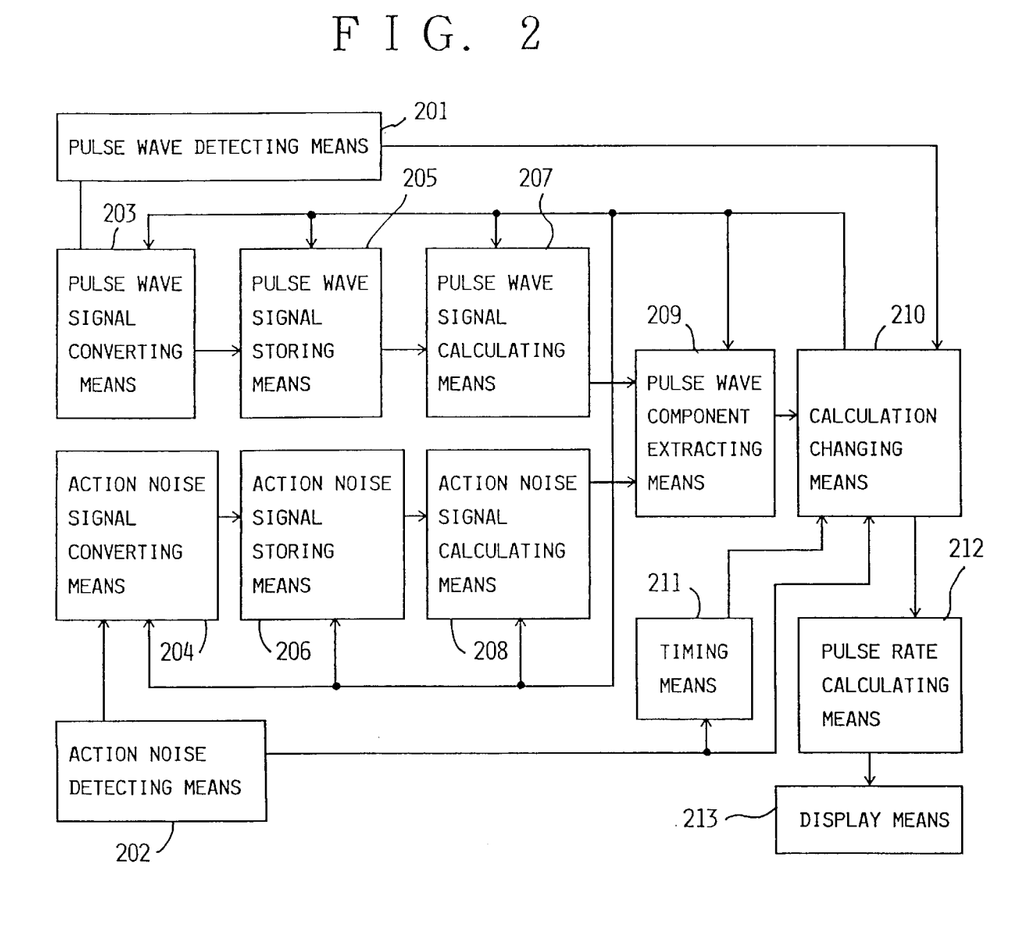
FIG. 2 is a functional block diagram for representing a second embodiment of the pulse rate monitor of the present invention.

FIG. 2 is a functional block diagram representing a second embodiment of the pulse rate monitor according to the present invention. Pulse wave signal converting means 203 converts an analog pulse wave voltage signal of a human body, detected by the pulse wave detecting means 201, into a digital signal. The converted digital signal is outputted into pulse wave signal storing means 205.

The action noise converting means 204 converts an analog voltage signal that is proportional to a magnitude of the action noise, detected by the action noise detecting means 202, into a digital signal. The converted digital signal is output into action noise signal storing means 206. The pulse wave signal storing means 205 stores therein the pulse wave signal converted into the digital signal. The action noise signal storing means 206 stores therein the action noise signal converted into the digital signal.

Pulse wave signal calculating means 207 sequentially reads out the pulse wave signals stored in the pulse wave signal storing means 205 and frequency-analyzes the read out pulse wave signals, thereby outputting the frequency-analyzed result into pulse wave component extracting means 209. Action noise signal calculating means 208 sequentially reads out the action noise signals stored in the action noise signal storing means 206 and performs a frequency analysis of the read out action noise signal, thereby outputting the frequency-analyzed result into the pulse wave component extracting means 209. The pulse wave component extracting means 209 extracts only the pulse wave components from the frequency-analyzed results by the pulse wave signal calculating means 207 and the action noise signal calculating means 208, thereby outputting these extracted pulse wave components to calculation changing means 210.

Timing means 211 counts a time period during which there is no action noise signal that has been rectangularized by the action noise detecting means 202, and informs when the counted time period exceeds a predetermined time period to the calculation changing means 210. Upon receipt of the "no action noise" indication issued from the timing means 211, the calculation changing means 210 outputs the pulse wave signal which has been rectangularized by the pulse wave detecting means 201 to the pulse rate calculating means 212. At the same time, the calculation changing means 210 stops the operations of these pulse wave signal converting means 203, pulse wave signal storing means 205, pulse wave signal calculating 207, action noise signal converting means 204, action noise signal storing means 206, action noise signal calculating means 208, and pulse wave component extracting means 209.

While the calculation changing means 210 outputs the rectangularized pulse wave signal to the pulse rate calculating means 212, when the action noise is detected by the action noise detecting means 202, the calculation changing means 210 immediately restarts the operations of the above described pulse wave signal converting means 203, pulse wave signal storing means 205, pulse wave signal calculating means 207, action noise signal converting means 204, action noise signal storing means 206, action noise signal calculating means 208, and pulse wave component extracting means 209, and also changes into the output signal of the pulse wave component extracting means 209.

In the pulse rate calculating means 212, a pulse rate is calculated from either the frequency component of the pulse wave extracted by the pulse wave component extracting means 209, or the periodic data of the pulse wave which has been rectangularized by the pulse wave detecting means 201, and the calculation result is output to the display means 213.

Figure 3:
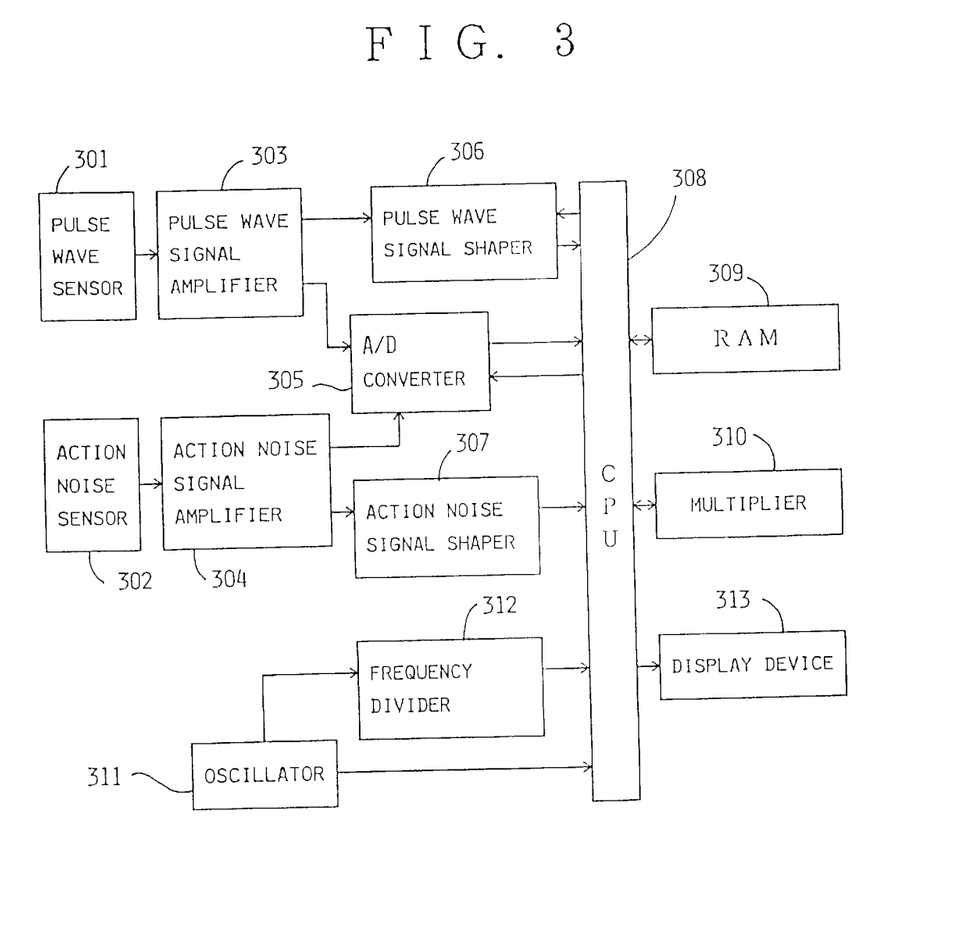
FIG. 3 is a functional block diagram for showing a pulse rate monitor according to third embodiment of the present invention.

FIG. 3 is a functional block diagram for representing a pulse rate monitor according to a third embodiment of the present invention. A pulse wave sensor 301 senses a pulse wave from a biological body, and outputs the sensed pulse wave signal to a pulse wave signal amplifier 303. An action noise sensor 302 senses movement of the biological body and outputs the sensed action noise signal to an action noise signal amplifier 304.

As the pulse wave sensor, for instance, a piezoelectric microphone is employed. As the action noise sensor, an acceleration sensor is utilized.

The pulse wave signal amplifier 303 amplifies the pulse wave signal and outputs the amplified pulse wave signal to an A/D converter 305 and a pulse wave shaper 306. The action noise signal amplifier 304 amplifies the action noise signal and outputs the amplified action noise signal to the A/D converter 305 and an action noise signal shaper 307. The A/D converter 305 converts both the pulse wave signal and the action noise signal to output the A/D-converted pulse wave signal and action noise signal to a CPU 308. The pulse wave signal shaper 306 shapes the pulse wave signal into a rectangular wave and outputs the shaped pulse wave signal to the CPU 308. The action noise signal shaper 307 shapes the action noise signal into a rectangular wave and outputs the shaped action noise signal to the CPU 308.

Figure 4:
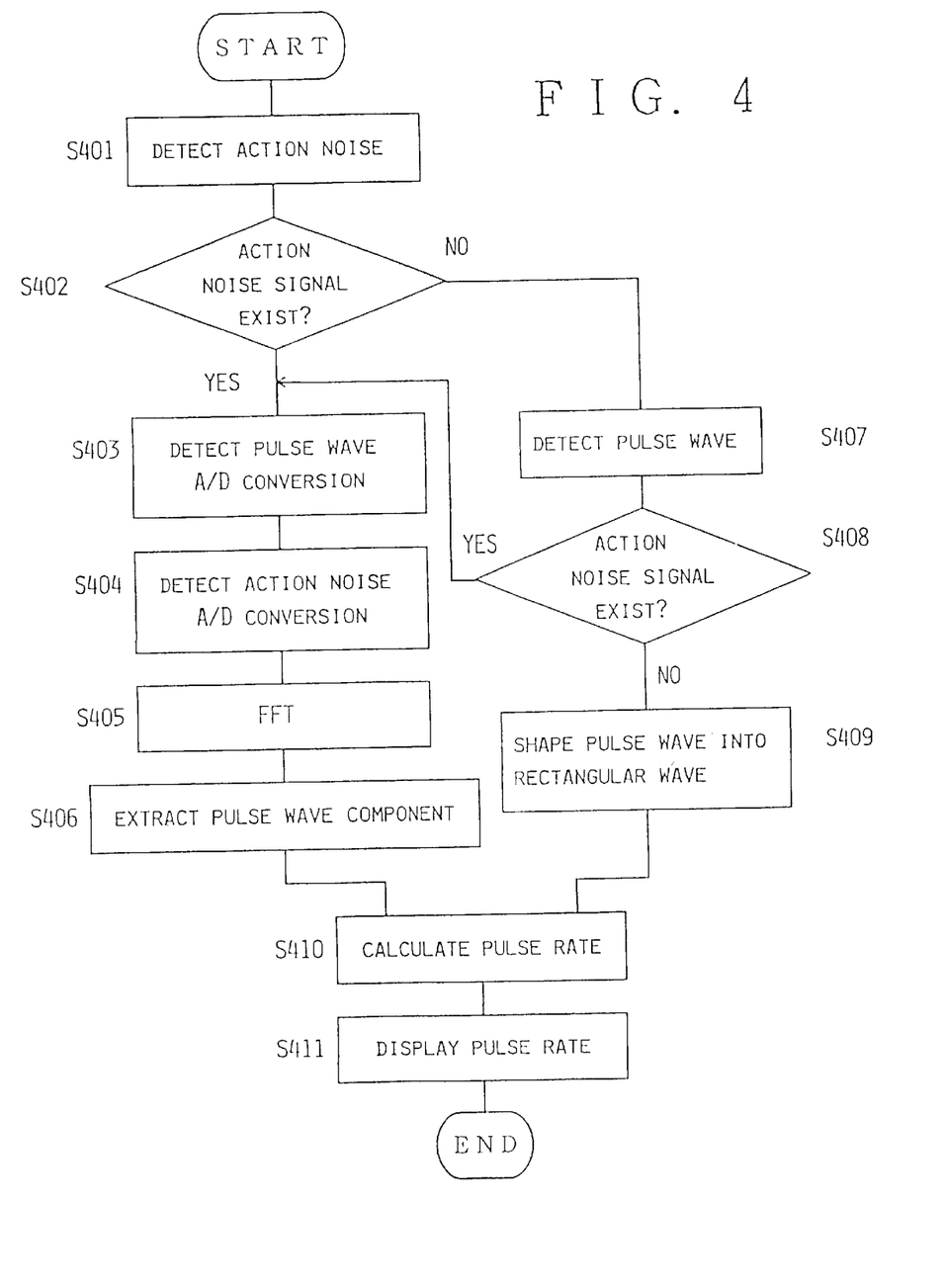
FIG. 4 is a flow charge for showing an operation concept of CPU in the pulse rate monitor according to the first through third embodiments of the present invention.

FIG. 4 is a flowchart representing a sequential operation in which a confirmation is made as to whether or not the action noise signal is present, the calculation method for the pulse wave signal is changed, and the pulse rate is calculated and then displayed. In FIG. 3 and FIG. 4, the CPU 308 confirms whether or not the action noise signal is present in response to the output signal issued from the action noise signal shaper 307, and then switches the calculation method (S402). When the existence of the action noise signal is confirmed (S402:YES), the CPU 308 performs an FFT process (S405) on the A/D-converted pulse wave signal (S403) and the A/D-converted action noise signal (S404), and further extracts the pulse wave frequency components (S406).

When the existence of the action noise signal is not confirmed (S402:NO), the pulse wave is detected (S407) and the pulse waveform is rectangular-converted (S409). During this process, another confirmation is made as to whether or not an action noise signal is present (S408). When there is still no action noise signal (S408:NO), the pulse rate is calculated directly from the rectangular wave (S410). At this time, in FIG. 3, since both the pulse wave signal and the action noise signal are no longer required for the A/D conversion, the operation of the A/D converter 305 is stopped and also the operation of the multiplier 310 is stopped which is required to perform the FFT process. Furthermore, the operation required to extract the pulse wave component extracted in the CPU 308 is stopped, so that total power consumption can be lowered.

When an action noise signal has been detected (S408:YES), the frequency analysis is carried out by the FFT process operation (S405), and the pulse rate is calculated from the extracted pulse wave component (S410).

Figure 5A:
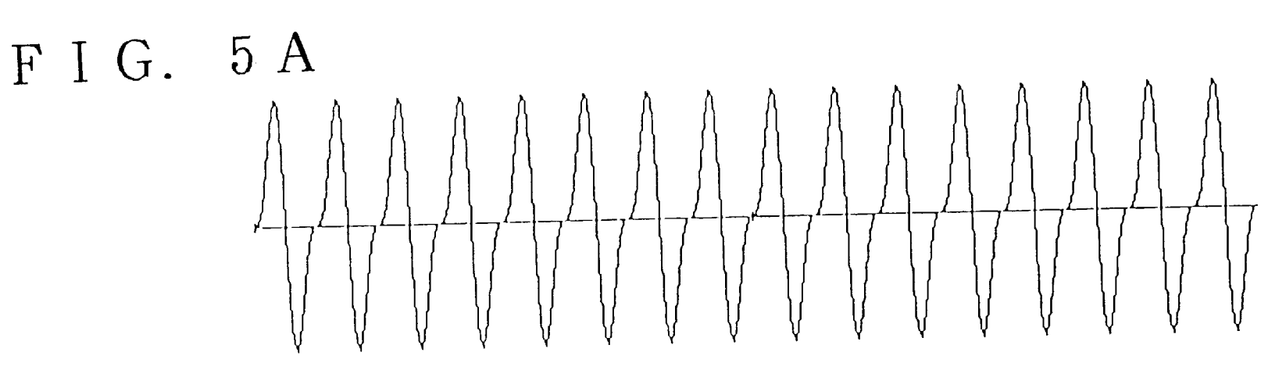
FIG. 5A shows an example of a waveform to be FFT-processed.
Figure 5B:
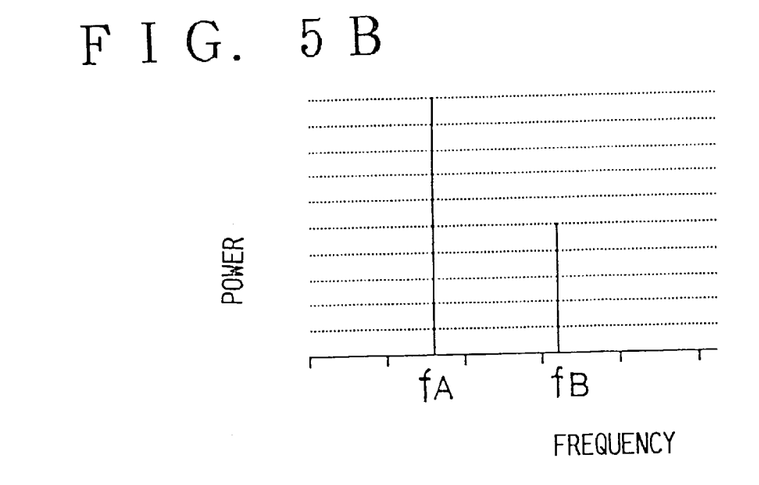
FIG. 5B indicates a result of the FFT-processed waveform.

In FIGS. 5A and 5B, there is graphically shown the result (FIG. 5B) obtained when a signal (FIG. 5A) including a frequency component fA and a frequency component fB equal to a half of the amplitude of the frequency component fA is FFT-processed. The lowest frequency obtained from the FFT-processed result is determined by the inverse number of the analyzing period of time. Assuming now that the analyzing period is 16 seconds, the line spectrum resolution becomes 1/16 seconds or 62.5 ms in period. As a consequence, the signal to be analyzed is resolved into such harmonic components being equal to 16 Hz multiplied by an integer. The magnitudes (power) of the respective harmonic components are denoted by a height in ordinate. In FIG. 5B, there is represented the state in which the power of the frequency component fB is equal to a half of the power of the frequency component fA.

Figure 6A:
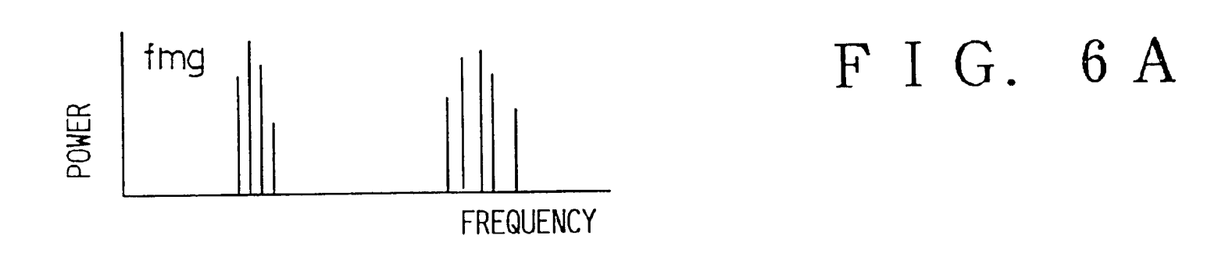
FIG. 6A shows a result of the FFT-processed output signal of the pulse wave sensor.
Figure 6B:
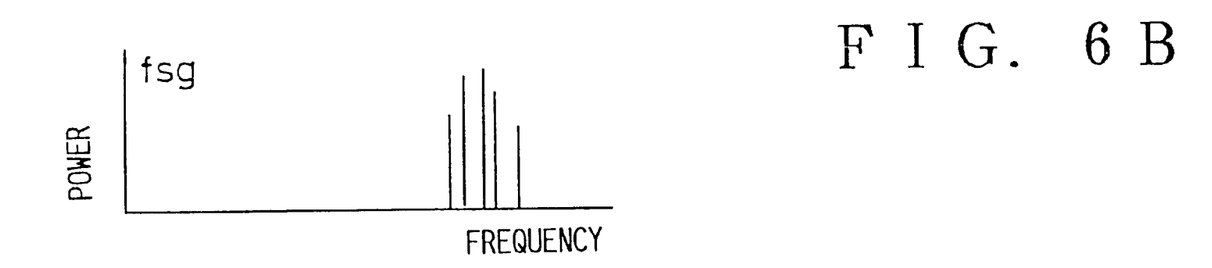
FIG. 6B indicates a result of the FFT-processed output signal of the action noise sensor.
Figure 6C:
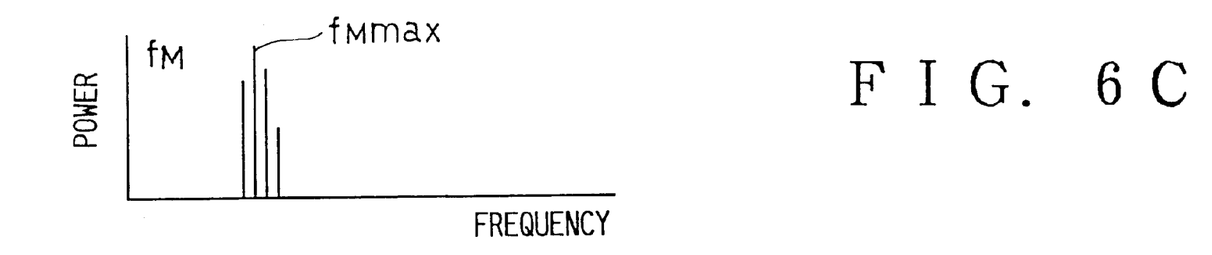
FIG. 6C represents such a pulse wave component obtained by subtracting the result of FIG. 6B from the result of FIG. 6A.

FIGS. 6A–6C show results obtained by FFT processing the output signals of the pulse wave sensor and the action noise sensor under an action condition. FIG. 6A represents a pulse wave spectrum "fmg", FIG. 6B indicates an action noise spectrum "fsg", FIG. 6C denotes a spectrum obtained by subtracting the action noise spectrum from the pulse wave spectrum, i.e., extracted pulse wave components "fM". As illustrated in FIG. 6A, both of the frequency components of the pulse waveform and the frequency components of the signal produced by the action are superimposed. On the other hand, since the action noise sensor responds only to the action of the biological body, frequency components of the signal produced only by the action are obtained. As a result, the spectrum fsg is subtracted from the spectrum fmg, so that among the remaining line spectrum components, the maximum power component is specified as the pulse wave frequency component. Based upon the frequency component of this pulse wave signal, the pulse rate is calculated (FIG. 4, S410) and the calculated pulse rate is outputted to a display element such as an LCD panel (S411).

Figure 7:
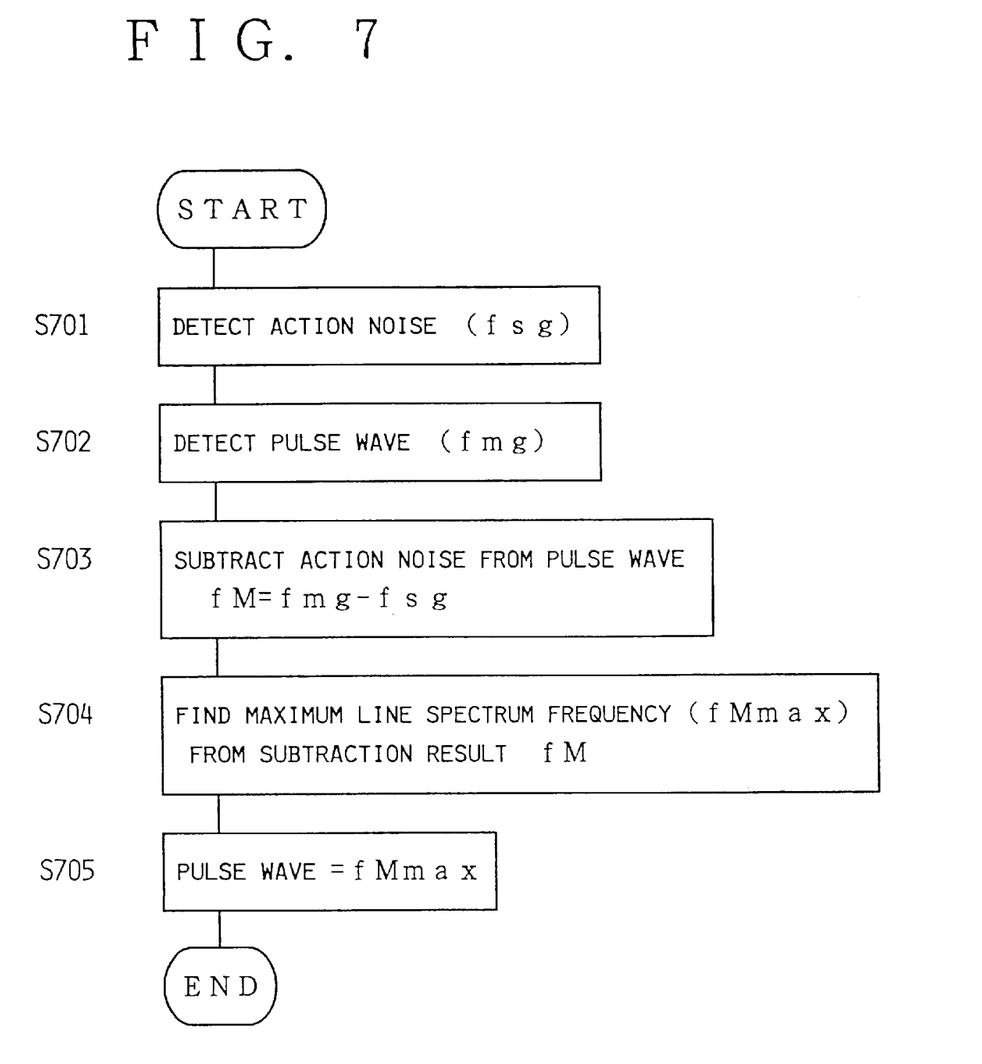
FIG. 7 is a flow chart for indicating one example of the method for specifying the pulse wave component of the pulse rate monitor according to the present invention.

The above-described method for specifying the pulse wave component is shown in FIG. 7. At step S703, the action noise spectrum is subtracted from the pulse wave spectrum (fM=fmg−fsg), whereby frequency components contained only in the pulse wave signal are derived. The maximum power frequency component among the derived pulse wave components fM is then determined (S704). The specified fMmax is the frequency component of the pulse wave.

Actually, there are some difficult cases in using such a subtracting method for subtracting those signal components. When the respective sensor output waveforms are frequency-analyzed, adverse influences are produced by the harmonic signals. As a consequence, a method for specifying a pulse wave will now be described in greater detail.

Figure 8:
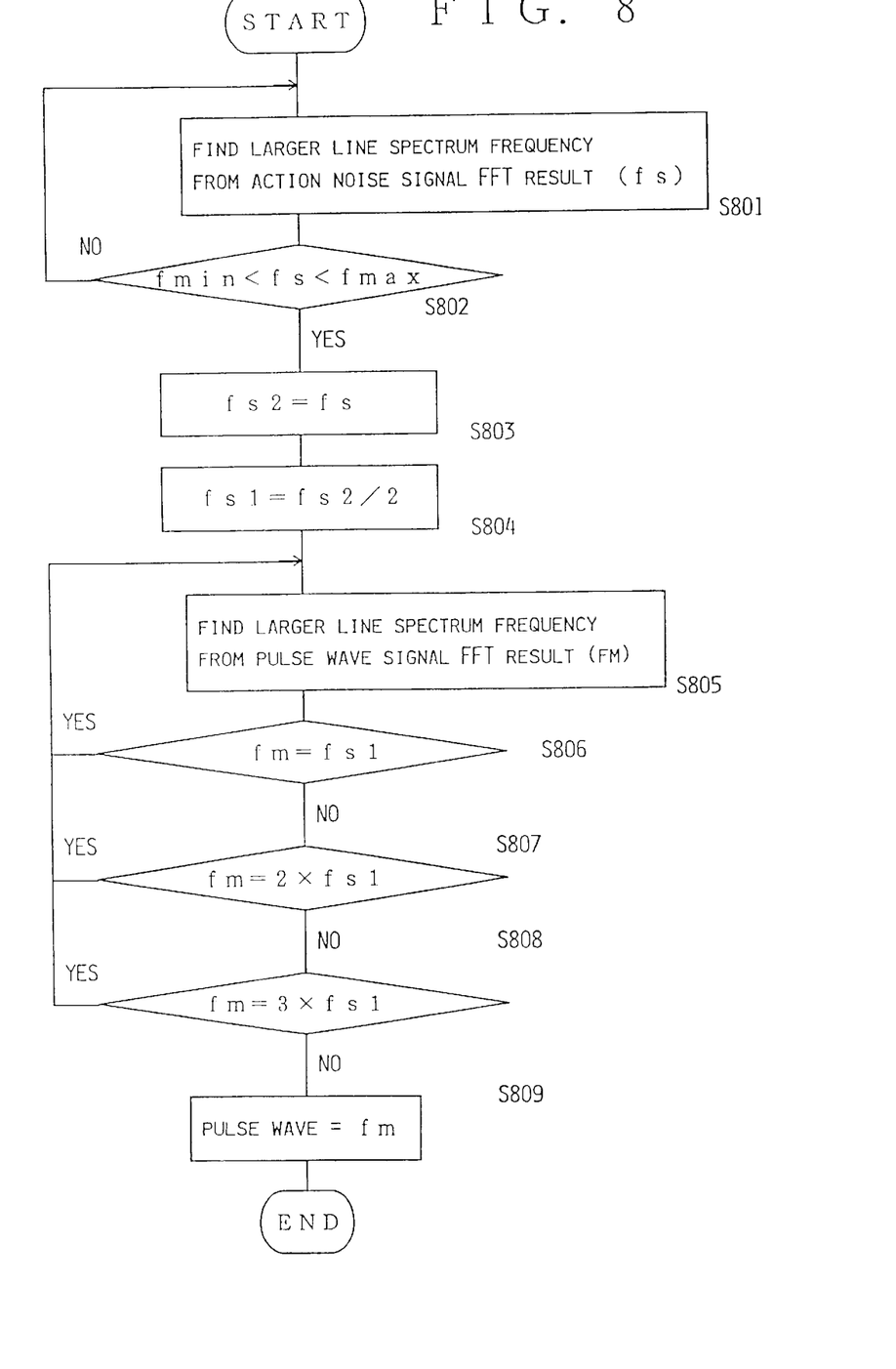
FIG. 8 is a flow chart for indicating one example of the pulse rate monitor according to the present invention.

In FIG. 8, there is shown a processing method for determining a pulse wave component after an action noise component is extracted from a signal of the action noise sensor, and the action noise component is eliminated from a frequency-analyzed result of a pulse wave signal. To extract the action noise component, at least one harmonic order of the action noise component is specified and then the other action noise components are calculated based upon the specified information of at least one harmonic order of the action noise. The second harmonic fs2 of the action noise sensor, which is relatively easy to detect, is specified at steps S801, S802, and S803. The pulse wave component extracting means 104 finds a larger line spectrum frequency (fs) from the action noise signal FFT result at step S801. At first, the largest line spectrum frequency from the action noise signal FFT result is selected. It is determined whether the frequency (fs) is within the range from fmin to fmax at step S802. Assuming now that the action noise is due to running, fmin of step S802 becomes 2 Hz corresponding to the lower limit frequency of the second harmonic appearing in the running noise signal. Symbol "fmax" is such a frequency determined by the sampling rate for the A/D conversion. Assuming now that the sampling frequency is 8 Hz, the maximum frequency at which the original waveform can be reproduced from the sampling theory is automatically determined as 4 Hz. Within a range from this fmax to fmin, the maximum line spectrum is specified as the second harmonic of the action noise component. If the frequency (fs) is out of range, the pulse wave component extracting means 104 finds the next frequency (fs) at step S801 and again determines whether it is within the range from fmin to fmax at step S802. The frequency found at step S802 is defined as the second harmonic of the action noise component at step S803. As described above, the pulse wave component extracting means 104 finds the second harmonic of the action noise component through steps S801 and S803. At step S804, the fundamental harmonic fs1 of the action noise component is obtained. The fundamental harmonic fs1 of the action noise component is calculated by dividing the second harmonic of the action noise component by two at step S804.

At the subsequent steps S805, S806, S807, and S808, pulse wave components coincident with the fundamental harmonic (fs1), the second harmonic (2×fs1), and the third harmonic (3×fs1) of the action noise component are eliminated, and the maximum frequency component among the remaining components is specified as a pulse wave "fm" at a step S809. Normally, the action noise frequency is 1 to 2 Hz. At first, the pulse wave component extracting means 104 finds a larger line spectrum frequency (fm) from the pulse wave signal FFT result at step S805.

It is determined whether the frequency (fm) is equal to the fundamental harmonic fs1 of the action noise component at step S806. When the frequency fm is equal to the frequency fs1, the pulse wave component extracting means 104 sets the frequency fm as the fundamental harmonic fs1 of the action noise component and then finds the next frequency fm at step S805. When the frequency fm is not equal to the frequency fs1, the pulse wave component extracting means 104 determines that the frequency fm is not the fundamental harmonic fs1 of the action noise component and then goes to step S807.

It is then determined whether the frequency fm is equal to the second harmonic of the action noise component at step S807. The second harmonic frequency is calculated by multiplying the fundamental frequency of the action noise signal by two. When the frequency fm is equal to the frequency (2×fs1), the pulse wave component extracting means 104 determines the frequency as the second harmonic of the action noise component and then finds the next frequency fm at step S805. When the frequency fm is not equal to the frequency (2×fs1), the pulse wave component extracting means 104 determines that the frequency fm is not the second harmonic of the action noise component and then goes to step S808.

It is determined whether or not the frequency fm is equal to the third harmonic of the action noise component at step S808. The third harmonic frequency is calculated by multiplying the fundamental frequency of the action noise signal by three. When the frequency fm is equal to the frequency (3×fs1), the pulse wave component extracting means 104 determines that the frequency fm is the third harmonic of the action noise component and then finds the next frequency fm at step S805. When the frequency fm is not equal to (3×fs1), the pulse wave component extracting means 104 determines that the frequency fm is not the third harmonic of the action noise component and then goes to step S809. The frequency determined at step S808 is defined as the fundamental harmonic of the pulse wave component at step S809.

As a result, when the maximum frequency component fmax is equal to 4 Hz, it is sufficient to check the harmonics up to the third harmonic.

Now, a description will be made of the reason why the maximum action noise component in the frequency region from 2 Hz to 4 Hz is extracted, and then this frequency is handled as the second harmonic of the action noise component in the above-described embodiment.

Figure 13:
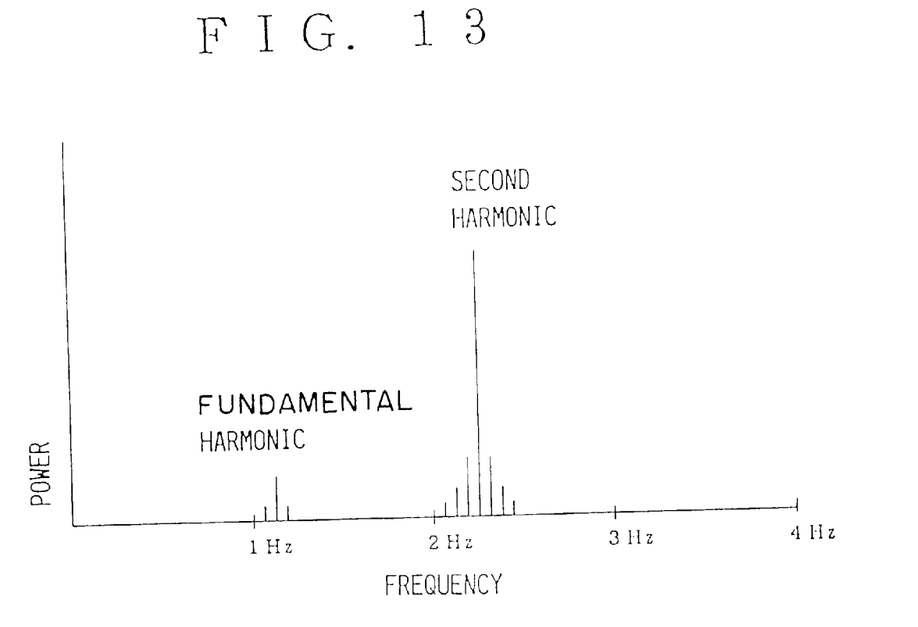
FIG. 13 represents a result of the FFT-processed output signal from the action noise sensor.

FIG. 13 schematically represents results obtained by FFT-processing the outputs of the action noise sensor. Generally speaking, under action condition, especially, under running condition, as illustrated in FIG. 13, higher power is observed in the second harmonic, as compared with that of the fundamental harmonic (i.e., 3 to 10 times higher than the fundamental harmonic during normal running). There are three sensing factors of the action noise sensor under running condition.

That is to say, (1) up/down movement under running condition,
(2) fundamental harmonic of arm swings, and
(3) second harmonic of arm swings.

As to the factor (1), since the up/down movement is equally performed when the right leg is stepped and the left leg is stepped, it becomes the second harmonic of the action noise components.

As to the factor (2), it is directed to such pendulum motion that the arm's pushing motion and the arm's pulling motion constitute one period. However, it is practically difficult that the arm swings under normal running are made as smooth pendulum motion, and therefore power of this component is weakened.

As to the factor (3), since acceleration is instantaneously applied to the arm's pushing motion and the arm's pulling motion, power of the second harmonic becomes higher than that of the fundamental harmonic. As a consequence, the second harmonic component among the action noise frequency component is emphasized.

Under normal running conditions, when the frequency range is selected from 2 Hz to 4 Hz, the range where the second harmonic appears can be covered, even if the running pace is increased and/or decreased. Therefore, the precision of detection may be increased by extracting the second harmonic component with the featured portion while limited to this frequency range.

Figure 9:
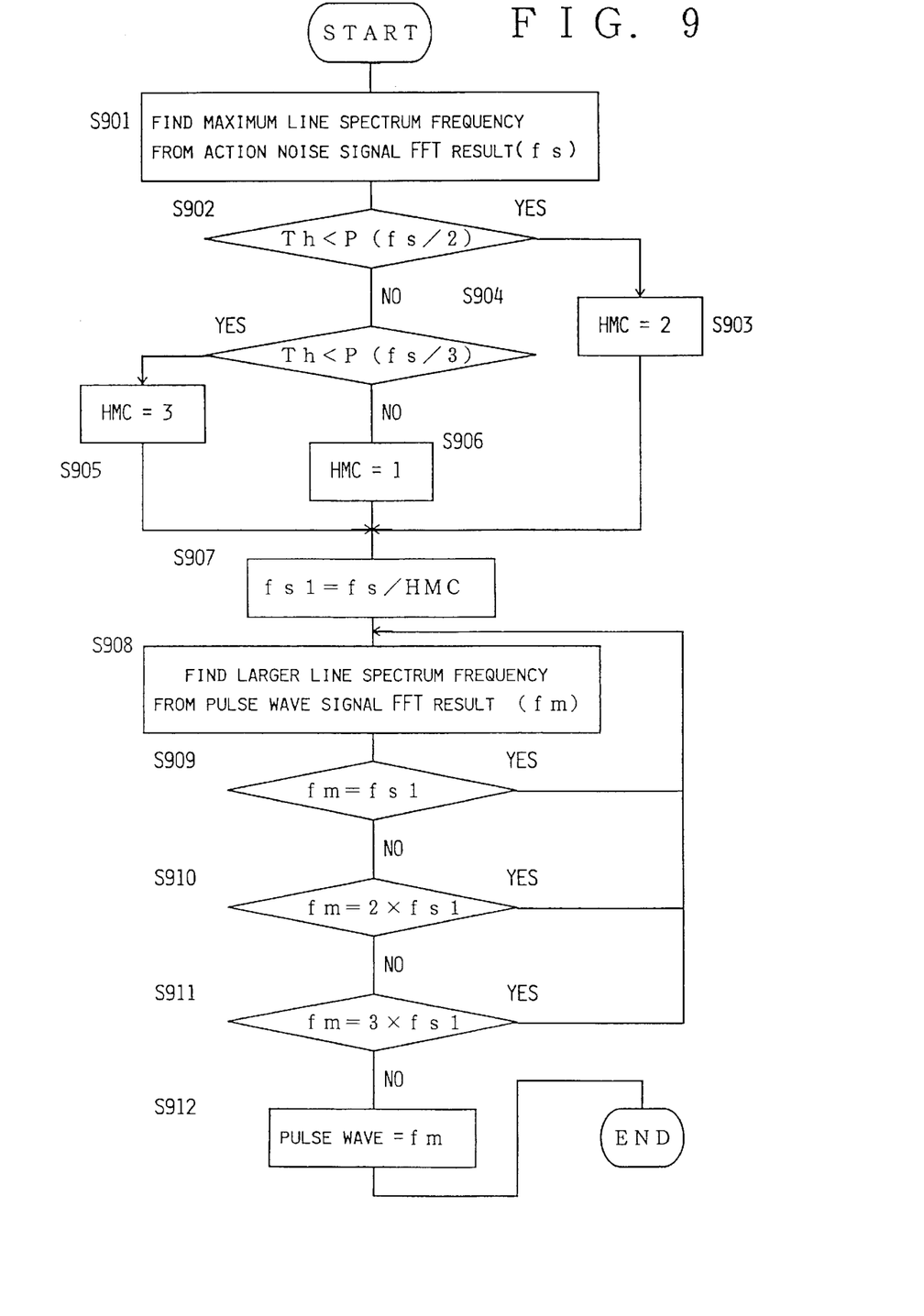
FIG. 9 is a flow chart for indicating one example of the method for specifying the pulse wave component of the pulse rate monitor according to the present invention.

In FIG. 9, there is shown a process for specifying a pulse wave component after a harmonic order of an action noise signal has been determined, or specified. At a step S901, a line spectrum fs in which power "P" is maximum is obtained from the frequency analyzed result of the action noise signal. Subsequently, a check is made as to whether or not an action noise component having a power higher than a predetermined value Th exists at a frequency equal to a half of fs (S902). When the line spectrum fs/2 is present (S902 YES), fs is specified as the second harmonic wave (HMC=2) (S903). When the line spectrum fs/2 is not present (S902:NO), another check is done as to whether or not an action noise component having a power higher than a predetermined value Th exists at a frequency equal to one third of fs at a step S904. When there is such an action noise component fs/3 (S904:YES), fs is specified as the third harmonic wave (HMC=3) (S905). If there is no action noise component fs/3 (S904:NO), then fs is specified as the fundamental harmonic fs1 (S906).

Since it could be specified in the above-described process operations that fs corresponds to one of the higher harmonics, the fundamental harmonic fs1 of the action noise signal is obtained at a step S907. A fundamental harmonic of action noise component (fs1) is calculated by dividing the line spectrum fs obtained at step S901 in to the harmonic order (HMC) specified at one of steps S903, S905 and S906. Then, at a step S908, the frequency component fm are successively compared with the action noise frequency in the order of the line spectrum with the higher power P from the frequency-analyzing results of the pulse waves. A check is done as to whether or not this frequency component is coincident with the fundamental harmonic (fs1) of the action noise signal, the second harmonic (2×fs1), and the third harmonic (3×fs1) (steps S908, S909, S910, and S911). With this process operation, the maximum pulse wave frequency component fm which is not coincident with the action noise components can be extracted at a step S912.

The frequency arrived at in step S911 is defined as the fundamental harmonic of the pulse wave component at step S912.

Figure 10:
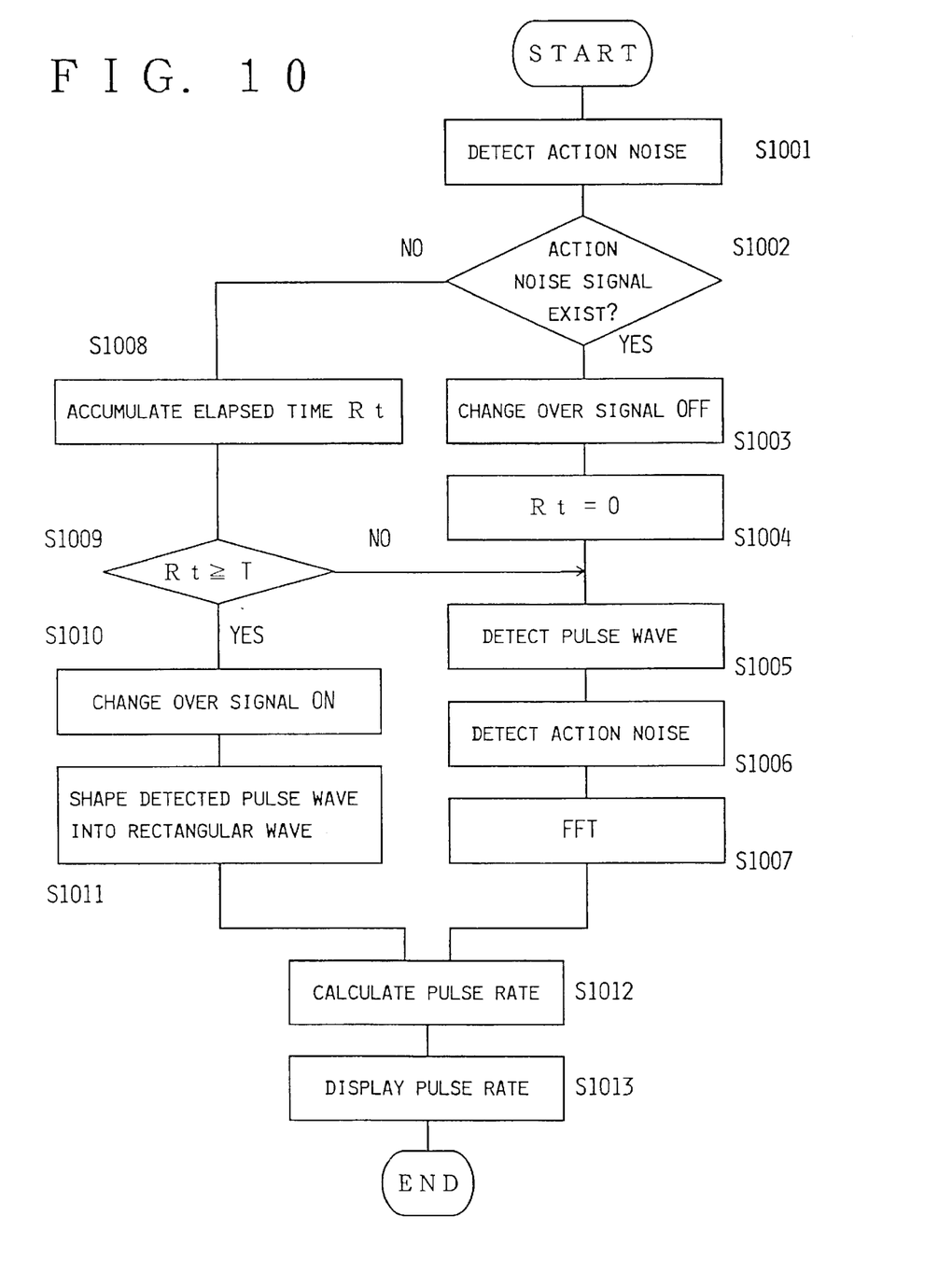
FIG. 10 is a flow chart for indicating one example of the method for specifying the pulse wave component of the pulse rate monitor according to the present invention.

FIG. 10 is a flow chart for representing a sequential operation in which a confirmation is made as to whether or not there is an action noise signal; when such a condition that the action noise signal is not confirmed exceeds a predetermined time "T", a calculation method is changed; and then a pulse rate is calculated based on a rectangular-shaped signal of pulse wave, and displayed. In FIG. 3 and FIG. 10, the CPU 308 makes a confirmation as to whether or not the action noise signal is present based on the output signal derived from the action noise signal shaper 307 (S1002). While the action noise signal is being confirmed (S1002:YES), a change over signal is set to OFF (S1003) so that accumulation time "Rt" for no action noise signal is set to zero (S1004). Thereafter, both the A/D converted action noise signal and pulse wave signal are FFT-processed to extract a pulse wave (S1007). Subsequently, a pulse rate is calculated (S1012) to be outputted to a display device 313 (S1013).

When no action noise signal is confirmed (S1002:NO), the time counting operation is commenced based on the output signal derived from an oscillator 311 and a frequency divider 312, so that elapsed time Rt is accumulated (S1008). When the accumulated time Rt exceeds a certain constant time T which is determined by either the sampling period of the signal used in the FFT process, or the sampling number (S1009:YES), the method for calculating the pulse rate is changed (S1010), the operations of the A/D conversion and the FFT process are stopped, and the pulse wave signal shaped by the pulse wave signal shaper 306 is entered to calculate the pulse rate (S1012). Then, the calculated pulse rate is outputted to the display device 313 (S1013).

Figure 14:
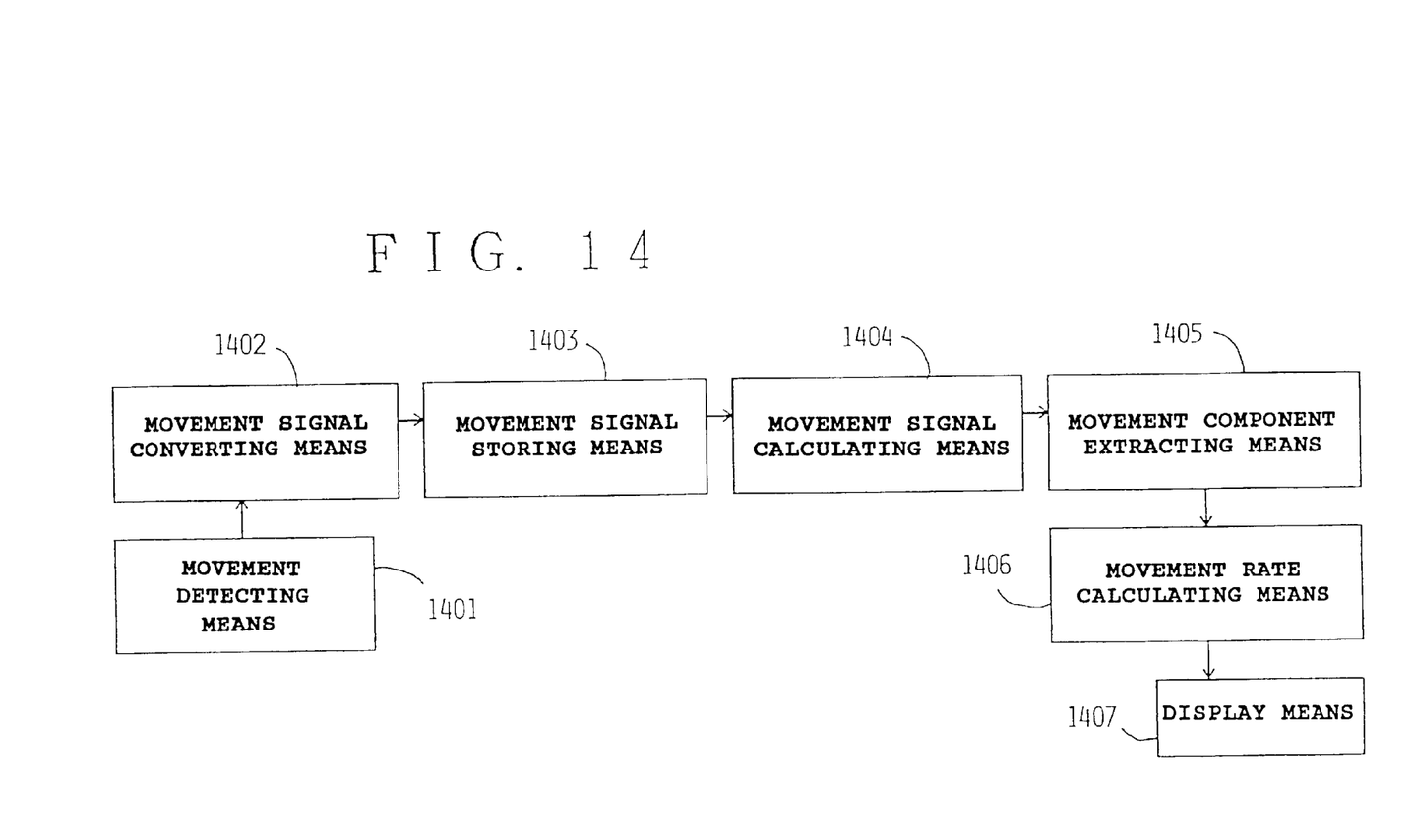
FIG. 14 represents an example of a functional structural diagram of a motion pitch monitor according to the present invention.

As previously described, there has been explained such an embodiment that the maximum pulse wave frequency component which is not coincident with the action noise component is specified to realize the pulse rate monitor. Alternatively, according to the present invention, it is possible to construct a high-precision movement rate monitor with employment of the completely same structure as above. In FIG. 14, there is shown a functional block diagram of an arrangement of a movement rate monitor. The frequency component of the movement rate is specified by action noise extracting means 1405. This specifying method may be readily realized by way of the methods previously described with reference to FIG. 8 and FIG. 9. In accordance with the movement rate monitor of the present invention, running speed, which is useful information for a runner, can be correctly obtained. Also, it may be possible to calculate a running distance based on the running pitches and the length of the user's stride.

Figure 12A:
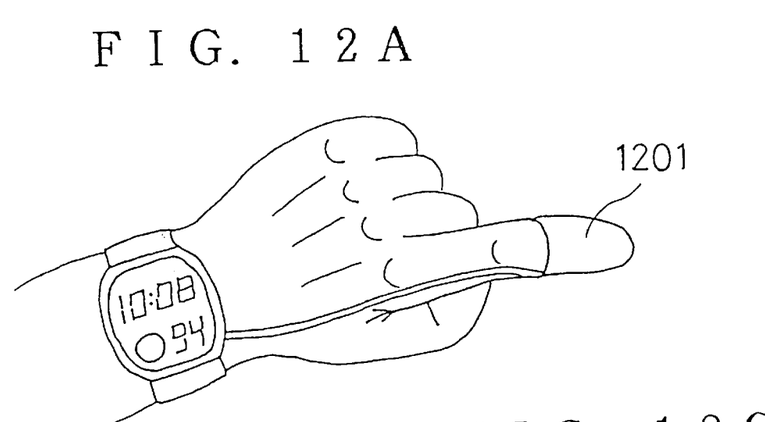
Figures 12B, 12C:
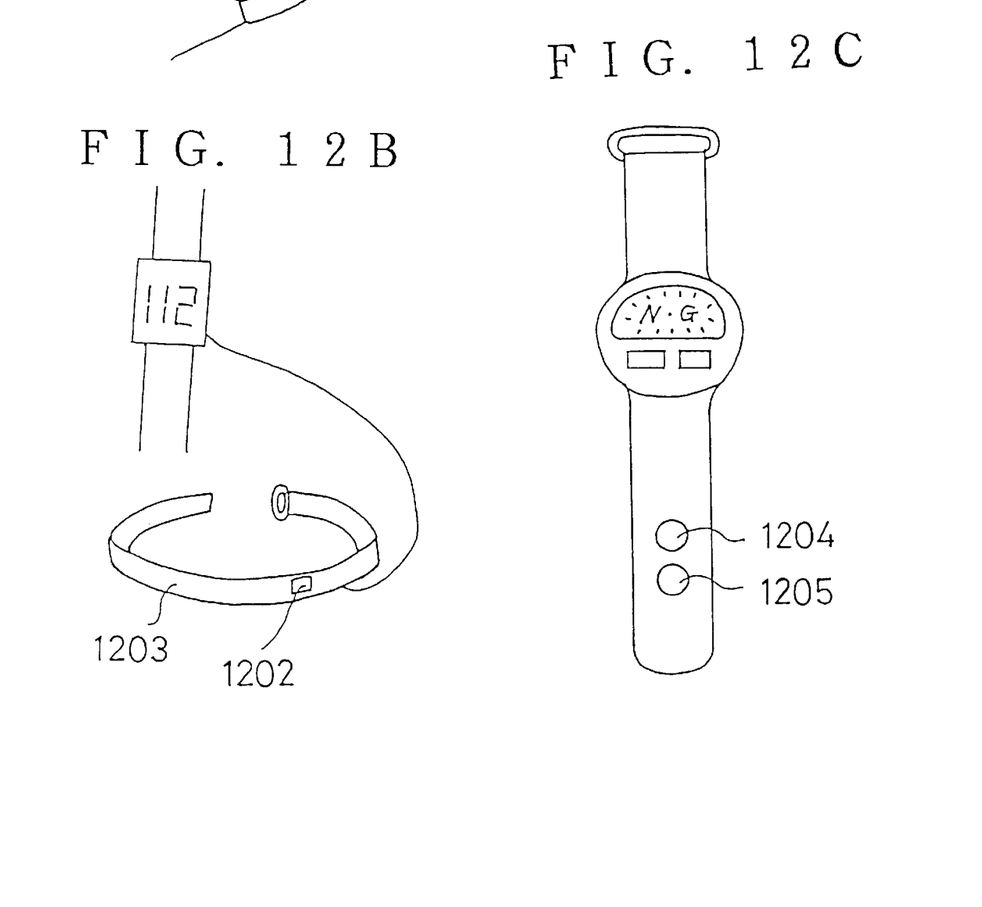

FIGS. 12A–12C are explanatory diagram for illustrating examples of outer appearance of the present invention. FIG. 12A indicates such a type of pulse rate monitor that the pulse wave sensor is assembled into a finger sack. FIG. 12B shows such a type of pulse rate monitor that an action noise sensor 1202 is assembled into a belt 1203. FIG. 12C indicates such a type of pulse wave monitor that both a pulse wave sensor 1204 and an action noise sensor 1205 are assembled into a wrist watchband in an integral form.

As previously described, according to the present invention, the pulse wave component extracting means is employed which extracts the pulse wave components from the respective frequency-analyzed results of the pulse wave sensor and the action noise sensor, so that the pulse rate during motion condition can be displayed. Furthermore, according to the present invention, under no motion condition where the frequency analyzing process operation is not required, the operations of the A/D converter and the calculating circuit can be stopped during which high power is consumed. Accordingly, the power consumption can be suppressed. Also, since a constant time required to perform the frequency analysis is prepared from the stationary condition until the calculation method is switched, so that noncontradictory process operation may be carried out and thus such a correct pulse rate can be displayed.

What is claimed is:

1. A movement monitor comprising:

movement detecting means for detecting movement of a biological body and outputting a corresponding movement signal that varies in accordance with the movement;

converting means for converting the movement signal into a digital signal;

storing means for storing the digital signal converted by the converting means;

movement signal calculating means for frequency-processing the digital signal stored in the storing means to obtain a set of movement components representing frequency versus power of the movement signal;

extracting means for extracting a selected component from the movement components; and calculating means for calculating a characteristic of the movement of the biological body based on the selected movement component extracted by the extracting means.

2. A movement rate monitor comprising:

movement detecting means for detecting movement of a biological body and outputting a corresponding movement signal which varies in accordance with a rate of the movement;

calculating means for frequency-processing the movement signal to obtain a spectrum of frequency components of the movement signal;

extracting means for extracting a selected component from the frequency components contained in the spectrum; and movement rate calculating means for calculating movement rate of the biological body based on the selected component extracted by the extracting means.

3. A movement rate monitor according to claim 2, further comprising converting means for converting the movement signal into a digital signal; and storing means for storing the digital signal converted by the converting means; wherein the calculating means frequency-processes the digital signal stored in the storing means to obtain the spectrum of frequency components of the movement signal.

4. A movement rate monitor according to claim 2, wherein the biological body is a human, the movement detecting means includes means for detecting movement associated with running, and the movement rate calculating means includes means for determining distance based upon a movement stride and a calculated movement rate.

* * * * *